United States Patent [19]

Hayakawa

[11] Patent Number: 5,527,492
[45] Date of Patent: Jun. 18, 1996

[54] COSMETIC AND DETERGENT PRODUCT COMPRISING HINOKITIOL AND A MIXTURE OF ANIONIC SURFACTANT AND AMPHOTERIC SURFACTANT

[75] Inventor: Ritsuko Hayakawa, Nagoya, Japan

[73] Assignee: Otsuka Pharmaceutical Co., Ltd., Tokyo, Japan

[21] Appl. No.: 203,763

[22] Filed: Mar. 1, 1994

Related U.S. Application Data

[63] Continuation of Ser. No. 855,630, filed as PCT/JP91/01129, Aug. 26, 1991, abandoned.

[30] Foreign Application Priority Data

| Sep. 14, 1990 | [JP] | Japan | 2-244182 |
| Dec. 6, 1990 | [JP] | Japan | 2-414153 |
| Apr. 5, 1991 | [JP] | Japan | 3-73053 |
| Jun. 10, 1991 | [JP] | Japan | 3-137622 |

[51] Int. Cl.$^6$ ............... C11D 1/10; C11D 1/94; C11D 3/33; C11D 3/48
[52] U.S. Cl. ............ 252/546; 252/106; 252/545; 252/547; 252/DIG. 5; 252/DIG. 13
[58] Field of Search ............... 252/106, 546, 252/545, DIG. 5, DIG. 13, 547

[56] References Cited

U.S. PATENT DOCUMENTS

| 3,957,970 | 5/1976 | Korkis | 424/70 |
| 4,147,782 | 4/1979 | Klein et al. | 424/230 |
| 4,181,634 | 1/1980 | Kennedy et al. | 252/545 |
| 4,361,581 | 11/1982 | Fukuda | 424/312 |
| 4,487,760 | 12/1986 | Yamamoto et al. | 424/70 |
| 5,084,212 | 1/1992 | Farris et al. | 252/544 |
| 5,156,836 | 10/1992 | Uchikawa et al. | 424/70 |

FOREIGN PATENT DOCUMENTS

| 46-4257 | 2/1971 | Japan . |
| 49-1718 | 1/1974 | Japan . |
| 54-043054 | 12/1979 | Japan . |
| 60-195200 | 10/1985 | Japan . |
| 62-5917 | 3/1987 | Japan . |
| 1-135712 | 5/1989 | Japan . |
| 1-117820 | 5/1989 | Japan . |
| 1-199916 | 8/1989 | Japan . |
| 1-199908 | 8/1989 | Japan . |
| 269411 | 3/1990 | Japan . |
| 2243607 | 9/1990 | Japan . |
| 363216 | 3/1991 | Japan . |

OTHER PUBLICATIONS

"Cosmedic", vol. 3, pp. 116–118, published Jan. 25, 1989 and English Translation.

Chemical Abstracts, vol. 109, 1988, 134816y, W. (A.M. Todd Co., Kalamazoo, MI), Dev. Food Sci.

Article from Kobe Newspaper, Nov. 14 (Wednesday), 1990 (and translation thereof).

Japanese Journal of Allergology, vol. 39, No. 9, 1990 (no month available).

English translation of JP 01/135712 May 1989.

English translation of JP 01/117820 May 1989.

English translation of JP 79/043054 Dec. 1979.

*Primary Examiner*—Erin M. Harriman
*Attorney, Agent, or Firm*—Sughrue, Mion, Zinn, Macpeak & Seas

[57] ABSTRACT

The invention provides a hypoirritant preservative for use in cosmetic and detergent products which comprises hinokitiol or a salt of hinokitiol and a detergent composition comprising an anionic surfactant or a salt thereof, an amphoteric surfactant and the above-mentioned preservative. The preservative of the invention is hypoirritant and the detergent composition of the invention, which contains the preservative, can be safely applied to the skin of human beings, particularly patients with atopic diseases of the skin.

21 Claims, No Drawings

COSMETIC AND DETERGENT PRODUCT COMPRISING HINOKITIOL AND A MIXTURE OF ANIONIC SURFACTANT AND AMPHOTERIC SURFACTANT

This is a continuation of application Ser. No. 07/855,630, filed as PCT/JP91/01129, Aug. 26, 1991, now abandoned.

TECHNICAL FIELD

The present invention relates to a hypoirritant preservative for use in cosmetics or detergent products for application in skin care and to a hypoirritant detergent composition.

BACKGROUND OF THE INVENTION

The conventional detergent or cleansing compositions (for example, shampoos) were highly irritant such that they facilitated itching or caused allergic reactions, with the result that they could not be used for patients with skin diseases, especially with sensitive skin such as atopic dermatitis, contact dermatitis, etc.

The object of the invention is to provide a hypoirritant detergent composition which can be safely used for patients with atopic dermatitis or the like skin diseases, particularly with sensitive skin to external irritants.

DISCLOSURE OF THE INVENTION

The present inventor has endeavored to accomplish the above object through intensive research. As a consequence, it has been found that hinokitiol or a salt thereof is extremely hypoirritant and has strong antiseptic activity, and that it is an excellent and useful preservative of the preparations such as cosmetics, detergents and other compositions which are in contact with the skin. It has also been discovered that when hinokitiol or a salt thereof, as a preservative, is used with at least one member selected from a hereindefined group of anionic surfactants and amphoteric surfactants, a markedly hypoirritant detergent composition can be made. The present invention has been developed on the basis of the above findings.

The present invention, therefore, provides:

a hypoirritant preservative for cosmetics and detergents which comprises hinokitiol or a salt thereof and a detergent composition containing at least one surfactant selected from the group consisting of anionic surfactants having the general formula

wherein $R^1$ is a saturated or unsaturated hydrocarbon radical having not more than 40 carbon atoms; $R^2$ is a lower alkyl radical; and A is a lower alkylene radical, inclusive of salts thereof, and amphoteric surfactants having the general formula

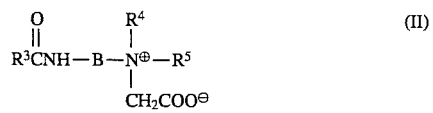

wherein $R^3$ is a saturated or unsaturated hydrocarbon radical having not more than 40 carbon atoms; and $R^4$ and $R^5$ each is a lower alkyl radical; and B is a lower alkylene radical and an antiseptic agent comprising hinokitiol or a salt thereof.

In this specification, the lower alkyl radical includes a straight-chain or branched-chain alkyl radical having 1 to 6 carbon atoms, such as methyl, ethyl, propyl, isopropyl, butyl, isobutyl, tert-butyl, pentyl, hexyl, etc. and a methyl radical as the most preferable radical.

The saturated or unsaturated hydrocarbon radical having not more than 40 carbon atoms includes, inter alia, methyl, ethyl, propyl, isopropyl, butyl, tert-butyl, pentyl, hexyl, heptyl, octyl, nonyl, decyl, undecyl, dodecyl, 11-methyldodecyl, 10-methylundecyl, tridecyl, tetradecyl, pentadecyl, heptadecyl, octadecyl, nonadecyl, eicosyl, heneicosyl, docosyl, tetracosyl, triacontyl, pentatriacontyl, tetracontyl, vinyl, allyl, isopropenyl, ethynyl, 2-pentynyl, 3-butenyl, 9-decenyl, cis-8-heptadecenyl, trans-8-heptadecenyl, 2-decynyl, 2-octynl, cocoalkyl and so on. Among these radicals, saturated or unsaturated hydrocarbon radicals having 5 to 19 carbon atoms are preferable and those having 7 to 13 carbon atoms are more preferable. Especially, as the radical shown by $R^1$ in general formula (I), a $C_{9-13}$ saturated hydrocarbon radical such as undecyl, tridecyl or the like, are preferable and the redical shown by $R^3$ in general formula (II), cocoalkyl and a $C_{9-13}$ saturated hydrocarbon radical such as undecyl, tridecyl or the like are preferable.

The lower alkylene radical includes a straight- or branched-chain alkylene radical having 1 to 6 carbon atoms, such as methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene and so on. As the radical represented by A in general formula (I), methylene and ethylene are favorable, and ethylene is more preferable. As the radical represented by B in general formula (II), ethylene and trimethylene are favorable and trimethylene is more preferable.

As the surfactant shown in general formula (I) and general formula (II), not only can the combination of surfactants having the same substituents be used, but also the combination of surfactants having different substituents.

The salts of compounds shown in general formula (I) include inorganic salts, e.g. salts with alkali metals such as sodium, potassium, etc., salts with alkaline earth metals such as magnesium etc., salts with other metals such as Cu, Zn, etc., ammonium salts, and organic salts, e.g. salts with alkanolamines such as diethanolamine, 2-amino-2-ethyl-1, 3-propanediol, triethanolamine, etc., salts with morpholine, piperazine, piperidine, etc. and salts with basic amino acids such as arginine, lysine, histidine and so on. The basic amino acids may be D-compounds or L-compounds or mixtures thereof.

The salt of hinokitiol may be any of the salts corresponding to the above-mentioned salts of compounds of general formula (I).

In the detergent composition or cleansing composition of the invention, the surfactant component is at least one surfactant selected from among anionic surfactants of general formula (I) and amphoteric surfactants of general formula (II). These surfactants not only have high detergent activity but are hypoirritant. In the practice of the present invention, the combined use of an anionic surfactant (I) and an amphoteric surfactant (II) is particularly preferred in that both the detergent action and hypoirritant feature of the resulting composition are markedly improved. In the case of such combined use, the weight ratio of surfactant (I) to surfactant (II) may be 1:20 through 20:1, preferably 4:1 through 1:3, and more preferably 4:1 through 3:2 and 3:2 through 2:3.

The proportion of the surfactant component in the detergent composition is not critical provided that a sufficient detergent effect can be insured. Generally, the proportion of the surfactant component as a whole is preferably 3 to 40 weight % and more preferably between 5 and 30 weight %.

The amount of hinokitiol or a salt thereof is not critical, either, provided that a sufficient preservative effect can be insured. Generally, this preservative is used preferably in a proportion of not less than 0,001 weight % and more preferably in a proportion ranging from 0,001 to 1.0 weight %, based on the total detergent composition.

The combined use of hinokitiol or a salt thereof, as a preservative, and the above-mentioned surfactant component gives a detergent composition with markedly hypoirritant, improved detergent action and strong antiseptic activity.

In the detergent composition of the invention, there may be further incorporated (1) a compound of the general formula

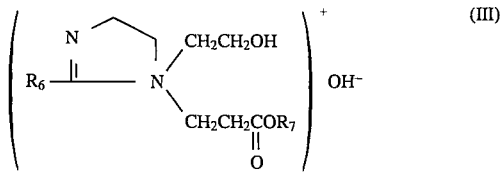

wherein $R_6$ is a saturated or unsaturated hydrocarbon radical having not more than 40 carbon atoms; $R_7$ is an alkali metal such as sodium, potassium, etc., an alkaline earth metal such as magnesium etc., or such a metal ion as copper, zinc, etc. or (2) an ordinary imidazolinium betaine type amphoteric surfactant such as Miranol C2M Conc., Miranol C2M Conc. NP, Miranol 2MCA Modified, Miranol HMS Conc. (all manufactured by Rhone Poulenc Surfactants & Specialities DIY. and marketed by Koei Perfumery Co., Ltd.). Addition of such a compound may alleviate the irritable reaction of the ocular mucosa. The preferred level of addition is about 10 to 200 percent by weight relative to the anionic surfactant of general formula (I).

The detergent composition of the invention can be provided and used within the ordinary pH range of cosmetic preparations, viz. generally pH about 6.0 to about 8.0 and preferably pH about 6.4 to about 7.5.

Where necessary and within the range not adversely affecting its performance, the detergent composition of the invention may contain other surfactants, oils such as higher alcohols, hair softeners such as cationized cellulose, humectants such as glycerol, propylene glycol, sorbitol, maltitol, etc., viscosity modifiers such as methylcellulose, hydroxymethylcellulose, hydroxyethylcellulose, carboxyvinyl polymer, polyvinyl alcohol, etc., film-forming agents such as hydrolyzed collagen, solvents such as ethanol, pH control agents such as citric acid, hydrochloric acid, etc., ultraviolet absorbers, antioxidants, sequestering agents, fungicides, preservatives, inorganic salts, antidandruff agents, vitamins, antiinflammatory agents and other pharmacologically active substances, animal or vegetable extracts, pigments, perfumes, etc. In using these additives, care is in order so that the addition thereof will not excessively increase the irritation level of the detergent composition. By way of illustration, when the detergent composition is intended for use by patients with atopic dermatitis, the final formulation preferably shows a dermal irritation index of not higher than about 15 as determined by the method described under the heading of Test Method which appears hereinafter. For use by healthy humans, the formulation preferably has a dermal irritation index of not more than about 30.

There is virtually no limitation on the form of the detergent composition of the invention. Thus, the composition can be used in a variety of known forms, such as liquid shampoos, creamy facial cleansers, facial gel cleansers, body shampoos, cleansing foams (in aerosol spray cans), detergents for dishwashing and other washing use, wet tissues and so on.

The detergent composition of the invention may be used as extemporaneously diluted with water where necessary. The detergent composition is not only extremely hypoirritant but also meets the essential requirements of a detergent, namely sufficient formability, detergency and so on. As such, this composition can be used not only for patients with atopic dermatitis or other diseases of the skin but also with advantage for healthy humans.

Hinokitiol, inclusive of salts thereof, is very low in the level of dermal irritation and is of value as a preservative for incorporation in a diversity of compositions destined to contact the skin, such as quasi drugs and various detergents for domestic use (e.g. shampoos for pet animals), toilet goods and so on.

EXAMPLES

The following examples are further illustrative of the present invention.

Example 1

A shampoo was prepared according to the following formula.

| | (W/W %) |
|---|---|
| Alaninate LN-30* | 40.0 |
| Swanol AM-3130N** | 10.0 |
| Hinokitiol | 0.02 |
| 99.5% Ethanol | 0.8 |
| pH control agent and sequestering agent | q.s. |
| Water to make 100 W/W % (pH 6.4) | |

*Alaninate LN-30: a surfactant based on N-lauroyl-N-methyl-β-alanine sodium, Nikko Chemicals
**Swanol AM-3130N: a surfactant based on cocofatty acid amide propyldimethylaminoacetic acid betaine, Nikko Chemicals The above shampoo was found to have satisfactory detergent activity. The dermal irritation potential of this composition was assessed by the following method.

Test method

Using the Finn chamber and Scanpor tape, a patch of filter paper imbibed with 1% aqueous solution of the above detergent composition was applied to the skin of 44 volunteers by the 48-hour occlusive dressing method and the dermal reaction was investigated at 1 and 24 hours after removal of the patch. The results were scored on the following scale.

| No reaction | 0 |
|---|---|
| Slight erythema | 0.5 |
| Definite erythema | 1.0 |
| Erythema with papules or edema | 2.0 |

Of the findings at 1 and 24 hours after removal, the result giving a higher score was taken, the sum of the scores was divided by the number of subjects, and the percentage of the quotient was used as the dermal irritation index.

As controls, the same dermal irritation test was carried out using 0.5% aqueous solution of sodium lauryl sulfate and purified water. The results are shown in Table 1.

TABLE 1

|  | Dermal irritation index |
| --- | --- |
| The composition of the invention | 6.8 |
| Aqueous sodium lauryl sulfate (0.5%) | 31.4 |
| Purified water | 5.7 |

It is apparent that the shampoo composition of the invention is extremely low in the irritation level.

Example 2

A body shampoo was prepared according to the following formula.

|  | (W/W %) |
| --- | --- |
| Alanon ACE** | 8 |
| Swanol AM-3130N | 4 |
| Hinokitiol triethanolamine salt | 0.05 |
| Nonionic surfactant** | 2 |
| Pearling agent*** | 2 |
| pH control agent | q.s. |
| Perfume | q.s. |
| Chelating agent | q.s. |
| Water to make 100 W/W % (pH 6.4) | |

*Alanon ACE: a surfactant based on N-cocoyl-N-methyl-β-alanine sodium, Kawaken Fine Chemical
**Nonionic surfactant: Emanon 3199 from Kao Corporation
***Pearling agent: Estepearl 15 from Nikko Chemicals Example 3

A facial cleanser was prepared according to the following formula.

|  | (W/W %) |
| --- | --- |
| Alanon ALE** | 5 |
| Swanol AM-3130N | 5 |
| Hinokitiol | 0.1 |
| 99.5% Ethanol | 1.0 |
| Nonionic surfactant** | 1.0 |
| Nonionic surfactant*** | 2.0 |
| pH control agent and glycerol | q.s. |
| Water to make 100 W/W % (pH 7.4) | |

*Alanon ALE: a surfactant based on N-lauroyl-N-methyl-β-alanine sodium, Kawaken Fine Chemical
**Nonionic surfactant: Amizet 5C, Kawaken Fine Chemical
***Nonionic surfactant: Emanon 3299, Kao Corporation Example 4

A swabbing composition was prepared according to the following formula.

|  | (W/W %) |
| --- | --- |
| Alaninate LN-30 | 2 |
| Alanon AME* | 1 |
| pH control agent | q.s. |
| Hinokitiol Na | 1 |
| 99% Ethanol | 3 |
| Water to make 100 W/W % (pH 7.0) | |

*Alanon AME: a surfactant based on N-myristoyl-N-methyl-β-alanine sodium, Kawaken Fine Chemical Example 5

A detergent composition for household ware was prepared according to the following formula.

|  | (W/W %) |
| --- | --- |
| Alanon ACE | 15 |
| Swanol AM-3130N | 5 |
| Hinokitiol triethanolamine salt | 0.01 |
| Hinokitiol L-arginine salt | 0.001 |
| pH control agent | q.s. |
| Color, perfume and glycerol | q.s. |
| Water to make 100 W/W % (pH 6.4) | |

Example 6

A body shampoo was prepared according to the following formula.

|  | (W/W %) |
| --- | --- |
| Nikkol Sarcosinate LK-30* | 10.0 |
| Swanol AM-3130N | 5.0 |
| Miranol C2M Conc.** | 10.0 |
| Hinokitiol | 0.01 |
| 99.5% Ethanol | 0.5 |
| pH control agent | q.s. |
| Water to make 100 W/W % (pH 7.5) | |

*Nikkol Sarcosinate LK-30: a surfactant based on potassium lauroylsarcosinate, Nikko Chemicals
**Miranol C2M Conc.: a surfactant based on cocoalkyl-N-carboxymethoxyethyl-N-carboxymethylimidazolinium disodium hydroxide, Koei Perfumery Co., Ltd.

Example 7

A facial cleanser was prepared according to the following formula.

|  | (W/W %) |
| --- | --- |
| Alaninate LN-30 | 30.0 |
| Swanol AM-3130N | 20.0 |
| Miranol C2M Conc. | 5.0 |
| Concentrated glycerol | 5.0 |
| Hinokitiol | 0.005 |
| 99.5% Ethanol | 0.2 |
| Pearling agent, thickener and pH control agent | q.s. |
| Water to make 100 W/W % (pH 6.8) | |

Example 8

A facial cleanser was prepared according to the following formula.

|  | (W/W %) |
| --- | --- |
| Alaninate LN-30 | 15.0 |
| Swanol AM 3130N | 10.0 |
| Miranol C2M Conc. | 2.0 |
| Hinokitiol triethanolamine salt | 0.005 |
| Pearling agent, pH control agent perfume and dye | q.s. |
| Water to make 100 W/W % (pH 7.5) | |

Example 9

A body shampoo was prepared according to the following formula.

|  | (W/W %) |
|---|---|
| Alaninate LN-30 | 15.0 |
| Swanol AM 3130N | 11.5 |
| Pearling agent, thickener, fat supplement, pH control agent chelating agent and humectant | q.s. |
| Hinokitiol morpholine salt | 0.02 |
| Water to make 100 W/W % (pH 6.8) | |

Examples 10 through 44

Using the compounds shown in Tables 2 through 4, the detergent compositions indicated in Table 5 (all figures are weight %) were prepared and the dermal irritation potential of each composition was evaluated. The same test method as described in Example 1 was used and the number of subjects was 20. The results as evaluated according to the following criteria are also shown in Table 5. As controls, the same test was performed using purified water and 0.5% aqueous solution of sodium lauryl sulfate. The results are shown in Table 6.

| Dermal irritation index ≦10 | − |
|---|---|
| Dermal irritation index 11–30 | + |
| Dermal irritation index ≧31 | ++ |

The results are shown in Table 7.

TABLE 2

Compounds of formula (I)

| No. | $R_1$ | $R_2$ | —A— | Salt |
|---|---|---|---|---|
| A-1 | $C_{11}H_{23}$ | $CH_3$ | —$(CH_2)_2$— | Sodium salt |
| A-2 | $C_{11}H_{23}$ | $CH_3$ | —$(CH_2)_2$— | Triethanolamine salt |
| A-3 | $C_{13}H_{27}$ | $CH_3$ | —$(CH_2)_2$— | Sodium salt |
| A-4 | $C_{11}H_{23}$ | $n$-$C_3H_7$ | —$(CH_2)_2$— | Sodium salt |
| A-5 | Mixture of $C_5H_{11}$—$C_{19}H_{39}$(n-Cocoyl) | $CH_3$ | —$(CH_2)_2$— | Sodium salt |
| A-6 | $C_{39}H_{79}$ | $CH_3$ | —$(CH_2)_2$— | Sodium salt |
| A-7 | $C_{11}H_{23}$ | $CH_3$ | —$CH_2$— | Sodium salt |
| A-8 | $C_5H_{11}$ | $CH_3$ | —$(CH_2)_2$— | Sodium salt |
| A-9 | $C_7H_{15}$ | $CH_3$ | —$(CH_2)_2$— | Sodium salt |
| A-10 | $C_{19}H_{39}$ | $CH_3$ | —$(CH_2)_2$— | Sodium salt |
| A-11 | $C_9H_{19}$ | $CH_3$ | —$(CH_2)_2$— | Sodium salt |

TABLE 3

Compounds of formula (II)

| No. | $R_1$ | $R_2$ | $R_5$ | B |
|---|---|---|---|---|
| B-1 | $C_{11}H_{23}$ | $CH_3$ | $CH_3$ | —$(CH_2)_3$— |
| B-2 | $C_{11}H_{23}$ | $C_2H_5$ | $C_2H_5$ | —$(CH_2)_3$— |
| B-3 | $C_{11}H_{23}$ | $CH_3$ | $CH_3$ | —$(CH_2)_2$— |
| B-4 | $C_{13}H_{27}$ | $C_2H_5$ | $C_2H_5$ | —$(CH_2)_2$— |
| B-5 | Mixture of $C_5H_{11}$—$C_{19}H_{39}$(n-Cocoyl) | $CH_3$ | $CH_3$ | —$(CH_2)_3$— |
| B-6 | $C_{39}H_{79}$ | $CH_3$ | $CH_3$ | —$(CH_2)_3$— |
| B-7 | $C_5H_{11}$ | $CH_3$ | $CH_3$ | —$(CH_2)_3$— |
| B-8 | $C_7H_{13}$ | $CH_3$ | $CH_3$ | —$(CH_2)_3$— |
| B-9 | $C_{19}H_{39}$ | $CH_3$ | $CH_3$ | —$(CH_2)_2$— |

TABLE 4

| No. | Hinokitiols |
|---|---|
| C-1 | Hinokitiol |
| C-2 | Hinokitiol.triethanolamine salt |
| C-3 | Hinokitiol.L-algininate |

TABLE 5

| | Example No. | | | | | |
|---|---|---|---|---|---|---|
| | 10 | 11 | 12 | 13 | 14 | 15 |
| A-1 | 15 | 10 | | 20 | | |
| A-2 | | | 5 | | | 7 |
| A-3 | | | | | | 3 |
| A-4 | | | | | 0.5 | |
| A-5 | | | | | | |
| A-6 | | | | | | |
| B-1 | | 10 | 15 | | 10 | |
| B-2 | | | | 1 | | |
| B-3 | | | | | | 3 |
| B-4 | | | | | | |
| B-5 | 5 | | | | | 7 |
| B-6 | | | | | | |
| C-1 | 0.005 | 0.01 | 0.05 | 0.01 | 0.001 | |
| C-2 | | | | | | 0.01 |
| C-3 | | | | | | |
| Ethanol | 0.1 | 0.1 | 0.5 | 0.2 | 0.05 | 0 |
| Water | To make 100 w/w % | | | | | |
| Dermal irritation index | — | — | — | — | — | — |

| | Example No. | | | | | |
|---|---|---|---|---|---|---|
| | 16 | 17 | 18 | 19 | 20 | 21 |
| A-1 | 10 | 10 | 10 | 10 | 15 | 10 |
| A-2 | | | | | | |
| A-3 | | 5 | | | | |
| A-4 | | | | | | |
| A-5 | | | | | | |
| A-6 | | 1 | | | | |
| B-1 | | | 10 | 10 | | |
| B-2 | | | | | | |
| B-3 | | | | | | |
| B-4 | 1 | | | | | |
| B-5 | 10 | | | | 5.0 | 10 |
| B-6 | | 1 | | | | |
| C-1 | | 0.01 | | 0.5 | 0.05 | 0.02 |
| C-2 | | | 0.1 | 0.5 | | |
| C-3 | 0.01 | | | | | |
| Ethanol | 0 | 0.2 | 0 | 1.0 | 1.0 | 1.0 |
| Water | To make 100 w/w % | | | | | |
| Dermal irritation index | — | — | — | — | — | — |

| | Example No. | | | | |
|---|---|---|---|---|---|
| | 22 | 23 | 24 | 25 | 26 |
| A-1 | 5.0 | 20.0 | | | 3.0 |
| A-2 | | | | 7.0 | |
| A-3 | | | | 3.0 | |
| A-4 | | | | | |
| A-5 | | | | | 7.0 |
| A-6 | | | | | |
| B-1 | | | | | |
| B-2 | | | | | |
| B-3 | | | | | |
| B-4 | | | | 3.0 | |
| B-5 | 15.0 | | 20.0 | 7.0 | 10.0 |
| B-6 | | | | | |
| C-1 | 0.001 | 0.05 | 0.05 | 0.005 | 0.05 |
| C-2 | | | | | |
| C-3 | | | | | |

TABLE 5-continued

| | | | | | |
|---|---|---|---|---|---|
| Ethanol | 1.0 | 1.0 | 1.0 | 1.0 | 1.0 |
| Water | | To make 100 w/w % | | | |
| Dermal irritation index | — | — | — | — | — |

| | Example No. | | | | |
|---|---|---|---|---|---|
| | 27 | 28 | 29 | 30 | 31 |
| A-1 | 2 | 1 | 3 | 17 | 22 |
| A-2 | | | | | |
| A-3 | | | | | |
| A-4 | | | | | |
| A-5 | | | | | |
| A-6 | | | | | |
| B-1 | | | | | |
| B-2 | | | | | |
| B-3 | | | | | |
| B-4 | | | | | |
| B-5 | 1 | 2 | 2 | 13 | 18 |
| B-6 | | | | | |
| C-1 | 0.02 | 0.02 | 0.02 | 0.02 | 0.02 |
| C-2 | | | | | |
| C-3 | | | | | |
| Ethanol | 0.1 | 0.8 | 0.8 | 0.8 | 0.8 |
| Water | | To make 100 w/w % | | | |
| Dermal irritation index | — | — | — | — | — |

| | Example No. | | | | | | |
|---|---|---|---|---|---|---|---|
| | 32 | 33 | 34 | 35 | 36 | 37 | 38 |
| A-1 | 12 | | | | | 12 | 12 |
| A-2 | | | | | | | |
| A-3 | | | | | | | |
| A-4 | | | | | | | |
| A-5 | | | | | | | |
| A-6 | | | | | | | |
| A-7 | | 12 | | | | | |
| A-8 | | | 12 | | | | |
| A-9 | | | | 12 | | | |
| A-10 | | | | | 12 | | |
| B-1 | | | | | | | |
| B-2 | | | | | | | |
| B-3 | | | | | | | |
| B-4 | | | | | | | |
| B-5 | 10 | 10 | 10 | 10 | 10 | | |
| B-6 | | | | | | | |
| B-7 | | | | | | 10 | |
| B-8 | | | | | | | 10 |
| B-9 | | | | | | | |
| C-1 | 1.0 | 0.02 | 0.02 | 0.02 | 0.02 | 0.02 | 0.02 |
| C-2 | | | | | | | |
| C-3 | | | | | | | |
| Ethanol | 0.8 | 0.8 | 0.8 | 0.8 | 0.8 | 0.8 | 0.8 |
| Water | | To make 100 w/w % | | | | | |
| Dermal irritation index | — | — | — | — | — | — | — |

| | Example No. | | | | | |
|---|---|---|---|---|---|---|
| | 39 | 40 | 41 | 42 | 43 | 44 |
| A-1 | 12 | | 2 | 4 | 20 | 1 |
| A-2 | | | | | | |
| A-3 | | | | | | |
| A-4 | | | | | | |
| A-5 | | | | | | |
| A-6 | | | | | | |
| A-7 | | | | | | |
| A-8 | | | | | | |
| A-9 | | | | | | |
| A-10 | | | | | | |
| A-11 | | 12 | | | | |
| B-1 | | | | | | |
| B-2 | | | | | | |
| B-3 | | | | | | |
| B-4 | | | | | | |
| B-5 | | | 3 | 1 | 1 | 20 |
| B-6 | | | | | | |
| B-7 | | | | | | |
| B-8 | | | | | | |
| B-9 | 10 | 10 | | | | |
| C-1 | 0.02 | 0.02 | 0.02 | 0.02 | 0.02 | 0.02 |
| C-2 | | | | | | |
| C-3 | | | | | | |
| Ethanol | 0.8 | 0.8 | 0.8 | 0.8 | 0.8 | 0.8 |
| Water | | To make 100 w/w % | | | | |
| Dermal irritation index | — | — | — | — | — | — |

| | Example No. | | |
|---|---|---|---|
| | 45 | 46 | 47 |
| A-1 | 12 | | |
| A-2 | | | |
| A-3 | | 12 | |
| A-4 | | | |
| A-5 | | | 12 |
| A-6 | | | |
| A-7 | | | |
| A-8 | | | |
| A-9 | | | |
| A-10 | | | |
| A-11 | | | |
| B-1 | | | |
| B-2 | | | |
| B-3 | | | |
| B-4 | | | |
| B-5 | 3 | 3 | 3 |
| B-6 | | | |
| B-7 | | | |
| B-8 | | | |
| B-9 | | | |
| C-1 | 1.0 | 0.02 | 0.02 |
| C-2 | | | |
| C-3 | | | |
| Ethanol | 0.8 | 0.8 | 0.8 |
| Water | | To make 100 w/w % | |
| Dermal irritation index | — | — | — |

TABLE 6

| | Dermal irritation index |
|---|---|
| Purified water | — |
| 0.5% aqueous solution of sodium lauryl sulfate | ++ |

TABLE 7

| Example | 10 | 11 | 18 | 19 | 20 | 21 | 22 | 23 |
|---|---|---|---|---|---|---|---|---|
| pH | 7.51 | 7.31 | 7.48 | 7.82 | 7.44 | 7.27 | 7.04 | 7.58 |

| Example | 24 | 26 | 27 | 28 | 29 | 30 | 31 | 32 |
|---|---|---|---|---|---|---|---|---|
| pH | 6.44 | 7.32 | 7.70 | 7.30 | 7.64 | 7.35 | 7.34 | 7.03 |

| Example | 33 | 41 | 42 | 43 | 44 |
|---|---|---|---|---|---|
| pH | 7.41 | 7.37 | 7.76 | 7.70 | 6.90 |

Example 45

A facial cleanser was prepared according to the following formula.

|  | (W/W %) |
| --- | --- |
| Alaninate LN-30 | 15.0 |
| Swanol AM 3130N | 10.0 |
| Miranol C2M Conc. | 2.0 |
| Hinokitiol | 0.04 |
| 99.5% Ethanol | 0.76 |
| Pearling agent, pH control agent and humectant | q.s. |
| Water to make 100 W/W % (pH 7.2) | |

Example 46

A body shampoo was prepared according to the following formula.

|  | (W/W %) |
| --- | --- |
| Alaninate LN-30 | 15.0 |
| Swanol AM 3130N | 11.5 |
| Miranol C2M Conc. | 2.5 |
| Hinokitiol | 0.04 |
| 99.5% Ethanol | 0.76 |
| Pearling agent, pH control agent and humectant | q.s. |
| Water to make 100 W/W % (pH 6.5) | |

Example 47

A shampoo composition was prepared according to the following formula.

|  | (W/W %) |
| --- | --- |
| Alaninate LN-30 | 40.0 |
| Swanol AM 3130N | 10.0 |
| Hinokitiol | 0.04 |
| 99.5% Ethanol | 0.76 |
| pH control agent and sequestering agent | q.s. |
| Water to make 100 W/W % (pH 6.4) | |

I claim:

1. A detergent composition comprising:
   (i) a mixture of an anionic surfactant and an amphoteric surfactant in an amount sufficient to provide a detergent effect, the anionic surfactant having the formula

(I)

wherein $R^1$ is a saturated or unsaturated hydrocarbon radical having 7 to 13 carbon atoms, and $R^2$ is a straight- or branched-chain alkyl radical having 1 to 6 carbon atoms or a salt thereof, the amphoteric surfactant having the formula

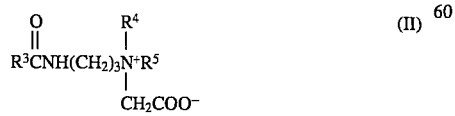

(II)

wherein $R^3$ is a saturated or unsaturated hydrocarbon radical having 7 to 13 carbon atoms, and $R^4$ and $R^5$ are each a straight- or branched-chain alkyl radical having 1 to 6 carbon atoms, and the weight ratio of the anionic surfactant to the amphoteric surfactant being 1:20 to 20:1, and (ii) 0.001 to 1.0 weight percent of hinokitiol or a salt thereof as an antiseptic agent.

2. A detergent composition according to claim 1 wherein the total amount of surfactants is 3 to 40% by weight.

3. A detergent composition according to claim 2 wherein the total amount of surfactants is 5 to 30% by weight.

4. A detergent composition according to claim 1, 2 or 3 wherein the anionic surfactant of formula (I) or a salt thereof is N-lauryl-N-methyl-β-alanine or a salt thereof and the amphoteric surfactant of formula (II) is cocofatty acid amide propyldimethylaminoacetic acid betaine.

5. A detergent composition according to claim 1, 2 or 3 which further contains an imidazolinium betaine type amphoteric surfactant selected from cocoalkyl-N-carboxymethoxyethyl-N-carboxymethylimidazolinium disodium hydroxide, 2-cocoalkyl-1-sodium carboxymethyloxyethyl-1-sodium carboxymethyl imidazolinium lauryl sulfate, and 2-lauryl-1-sodium carboxymethoxyethyl-1-sodium carboxymethyl imidazolinium dodecanoyl sarcosine, and wherein the proportion of said imidazolinium betaine type amphoteric surfactant is 10 to 200 weight percent of said anionic surfactant of formula (I).

6. A detergent composition according to claim 4 which further contains an imidazolinium betaine type amphoteric surfactant selected from cocoalkyl-N-carboxymethoxyethyl-N-carboxymethylimidazolinium disodium hydroxide, 2-cocoalkyl-1-sodium carboxymethyloxyethyl-1-sodium carboxymethyl imidazolinium lauryl sulfate, and 2-lauryl-1-sodium carboxymethoxyethyl-1-sodium carboxymethyl imidazolinium dodecanoyl sarcosine, and wherein the proportion of said imidazolinium betaine type amphoteric surfactant is 10 to 200 weight percent of said anionic surfactant of formula (I).

7. A detergent composition according to claim 6 wherein the imidazolinium betaine type amphoteric surfactant is cocoalkyl-N-carboxymethoxyethyl-N-carboxymethylimidazolinium disodium hydroxide.

8. A detergent composition for patients having atopic dermatitis, said composition comprising:
   (i) a mixture of an anionic surfactant and an amphoteric surfactant in an amount sufficient to provide a detergent effect, the anionic surfactant having the formula

(I)

wherein $R^1$ is a saturated or unsaturated hydrocarbon radical having 7 to 13 carbon atoms, and $R^2$ is a straight- or branched-chain alkyl radical having 1 to 6 carbon atoms or a salt thereof, the amphoteric surfactant having the formula

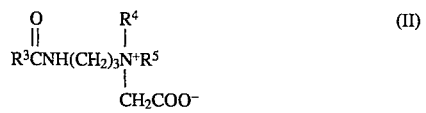

(II)

wherein $R^3$ is a saturated or unsaturated hydrocarbon radical having 7 to 13 carbon atoms, and $R^4$ and $R^5$ are each a straight- or branched-chain alkyl radical having 1 to 6 carbon atoms, and the weight ratio of the anionic surfactant to the amphoteric surfactant is from 1:20 to 20:1, and (ii) 0.001 to 1.0 weight percent of hinokitiol or a salt thereof as an antiseptic agent.

9. A detergent composition for patients having atopic dermatitis according to claim 8 wherein the total amount of surfactants is 3 to 40% by weight.

10. A detergent composition for patients having atopic dermatitis according to claim 9 wherein the total amount of surfactants is 5 to 30% by weight.

11. A detergent composition for patients having atopic dermatitis according to claim 8, 9 or 10 wherein the anionic surfactant of formula (I) or a salt thereof is N-lauryl-N-methyl-β-alanine or a salt thereof and the amphoteric surfactant of formula (II) is cocofatty acid amide propyldimethylaminoacetic acid betaine.

12. A detergent composition for patients having atopic dermatitis according to claim 8, 9 or 10 which further contains an imidazolinium betaine type amphoteric surfactant selected from cocoalkyl-N-carboxymethoxyethyl-N-carboxymethylimidazolinium disodium hydroxide, 2-cocoalkyl-1-sodium carboxymethyloxyethyl-1-sodium carboxymethyl imidazolinium lauryl sulfate, and 2-lauryl-1-sodium carboxymethoxyethyl-1-sodium carboxymethyl imidazolinium dodecanoyl sarcosine, and wherein the proportion of said imidazolinium betaine type amphoteric surfactant is 10 to 200 weight percent of said anionic surfactant of formula (I).

13. A detergent composition for patients having atopic dermatitis according to claim 11 which further contains an imidazolinium betaine type amphoteric surfactant selected from cocoalkyl-N-carboxymethoxyethyl-N-carboxymethylimidazolinium disodium hydroxide, 2-cocoalkyl-1-sodium carboxymethyloxyethyl-1-sodium carboxymethyl imidazolinium lauryl sulfate, and 2-lauryl-1-sodium carboxymethoxyethyl-1-sodium carboxymethyl imidazolinium dodecanoyl sarcosine, and wherein the proportion of said imidazolinium betaine type amphoteric surfactant is 10 to 200 weight percent of said anionic surfactant of formula (I).

14. A detergent composition for patients having atopic dermatitis according to claim 13 wherein the imidazolinium betaine type amphoteric surfactant is cocoalkyl-N-carboxymethoxyethyl-N-carboxymethylimidazolinium disodium hydroxide.

15. A method for cleansing the skin of patients with atopic dermatitis using a detergent composition comprising:

(i) a mixture of an anionic surfactant and an amphoteric surfactant in an amount sufficient to provide a detergent effect, the anionic surfactant having the formula

wherein $R^1$ is a saturated or unsaturated hydrocarbon radical having 7 to 13 carbon atoms, and $R^2$ is a straight- or branched-chain alkyl radical having 1 to 6 carbon atoms or a salt thereof, the amphoteric surfactant having the formula

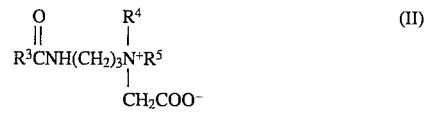

wherein $R^3$ is a saturated or unsaturated hydrocarbon radical having to 13 carbon atoms, and $R^4$ and $R^5$ are each a straight- or branched-chain alkyl radical having 1 to 6 carbon atoms, and the weight ratio of the anionic surfactant to the amphoteric surfactant is from 1:20 to 20:1, and (ii) 0.001 to 1.0 weight percent of hinokitiol or a salt thereof as an antiseptic agent.

16. A method according to claim 15 wherein the total amount of surfactants is 3 to 40% by weight.

17. A method according to claim 16 wherein the total amount of surfactants is 5 to 30% by weight.

18. A method according to claim 15, 16 or 17 wherein the anionic surfactant of formula (I) or a salt thereof is N-lauryl-N-methyl-β-alanine or a salt thereof and the amphoteric surfactant of formula (II) is cocofatty acid amide propyldimethylaminoacetic acid betaine.

19. A method according to claim 15, 16 or 17 wherein the detergent composition further contains an imidazolinium betaine type amphoteric surfactant selected from cocoalkyl-N-carboxymethoxyethyl-N-carboxymethylimidazolinium disodium hydroxide, 2-cocoalkyl-1-sodium carboxymethyloxyethyl-1-sodium carboxymethyl imidazolinium lauryl sulfate, and 2-lauryl-1-sodium carboxymethoxyethyl-1-sodium carboxymethyl imidazolinium dodecanoyl sarcosine, and wherein the proportion of said imidazolinium betaine type amphoteric surfactant is 10 to 200 weight percent of said anionic surfactant of formula (I).

20. A method according to claim 19 wherein the detergent composition further contains an imidazolinium betaine type amphoteric surfactant selected from cocoalkyl-N-carboxymethoxyethyl-N-carboxymethylimidazolinium disodium hydroxide, 2-cocoalkyl-1-sodium carboxymethyloxyethyl-1-sodium carboxymethyl imidazolinium lauryl sulfate, and 2-lauryl-1-sodium carboxymethoxyethyl-1-sodium carboxymethyl imidazolinium dodecanoyl sarcosine, and wherein the proportion of said imidazolinium betaine type amphoteric surfactant is 10 to 200 weight percent of said anionic surfactant of formula (I).

21. A method according to claim 20 wherein the imidazolinium betaine type amphoteric surfactant is cocoalkyl-N-carboxymethoxyethyl-N-carboxymethylimidazolinium disodium hydroxide.

* * * * *